(12) United States Patent
Biberger et al.

(10) Patent No.: US 8,893,651 B1
(45) Date of Patent: Nov. 25, 2014

(54) PLASMA-ARC VAPORIZATION CHAMBER WITH WIDE BORE

(75) Inventors: Maximilian A. Biberger, Scottsdale, AZ (US); Frederick P. Layman, Carefree, AZ (US)

(73) Assignee: SDCmaterials, Inc., Tempe, AZ (US)

(*) Notice: Subject to any disclaimer, the term of this patent is extended or adjusted under 35 U.S.C. 154(b) by 1463 days.

(21) Appl. No.: 12/151,830

(22) Filed: May 8, 2008

Related U.S. Application Data

(60) Provisional application No. 60/928,946, filed on May 11, 2007.

(51) Int. Cl.
*B01J 19/08* (2006.01)

(52) U.S. Cl.
USPC .................................................. 118/723 DC

(58) Field of Classification Search
USPC .................................................. 118/723 DC
See application file for complete search history.

(56) References Cited

U.S. PATENT DOCUMENTS

| | | | |
|---|---|---|---|
| 2,284,554 A | 5/1942 | Beyerstedt | |
| 2,419,042 A | 4/1947 | Todd | 202/205 |
| 2,519,531 A | 8/1950 | Worn | 230/95 |
| 2,562,753 A | 7/1951 | Trost | |
| 2,689,780 A | 9/1954 | Rice | 23/106 |
| 3,001,402 A | 9/1961 | Koblin | 73/421.5 |
| 3,042,511 A | 7/1962 | Reding, Jr. | |
| 3,067,025 A | 12/1962 | Chisholm | |
| 3,145,287 A * | 8/1964 | Seibein et al. | 219/75 |
| 3,178,121 A | 4/1965 | Wallace, Jr. | |
| 3,179,782 A * | 4/1965 | Matvay | 219/76.16 |
| 3,181,947 A | 5/1965 | Vordahl | |
| 3,313,908 A * | 4/1967 | Unger et al. | 219/76.16 |
| 3,401,465 A | 9/1968 | Larwill | |
| 3,450,926 A | 6/1969 | Kiernan | |
| 3,457,788 A | 7/1969 | Nobuo Miyajima | 73/422 |
| 3,537,513 A | 11/1970 | Austin et al. | 165/70 |

(Continued)

FOREIGN PATENT DOCUMENTS

| | | |
|---|---|---|
| EP | 1 134 302 A1 | 9/2001 |
| EP | 1 619 168 A1 | 1/2006 |

(Continued)

OTHER PUBLICATIONS

Nagai, Yasutaka, et al., "Sintering Inhibition Mechanism of Platinum Supported on Ceria-based Oxide and Pt-oxide—support Interaction," Journal of Catalysis 242 (2006), pp. 103-109, Jul. 3, 2006, Elsevier.

(Continued)

*Primary Examiner* — Erin Snelting
(74) *Attorney, Agent, or Firm* — Morrison & Foerster LLP

(57) ABSTRACT

A plasma-arc vaporization chamber includes features configured to permit very high-energy plasmas, preferably with high hydrogen content. The vaporization chamber includes a female electrode having an internal chamber with a target region made of a conductive material highly resistant to thermal degradation and an isthmus region of sufficient width to slow plasma flow therethrough enough to permit vaporization within the internal chamber of a material delivered into the plasma. The material is preferably injected at an angle counter to the flow of the plasma. The vaporization chamber also includes a flange-cooling chamber adjacent to a flange of the female electrode. Additionally, the chamber preferably includes vortexing gas injectors configured to provide a helical gas flow within at least a portion of the internal chamber.

11 Claims, 4 Drawing Sheets

(56) References Cited

U.S. PATENT DOCUMENTS

| | | | |
|---|---|---|---|
| 3,552,653 A | 1/1971 | Inoue | |
| 3,617,358 A | 11/1971 | Dittrich | |
| 3,667,111 A | 6/1972 | Chartet | |
| 3,741,001 A | 6/1973 | Fletcher et al. | 73/28 |
| 3,752,172 A | 8/1973 | Cohen et al. | |
| 3,761,360 A | 9/1973 | Auvil et al. | |
| 3,774,442 A | 11/1973 | Gustavsson | 73/28 |
| 3,804,034 A | 4/1974 | Stiglich, Jr. | |
| 3,830,756 A | 8/1974 | Sanchez et al. | |
| 3,871,448 A | 3/1975 | Vann et al. | |
| 3,892,882 A | 7/1975 | Guest et al. | |
| 3,914,573 A | 10/1975 | Muehlberger | |
| 3,959,094 A | 5/1976 | Steinberg | |
| 3,959,420 A | 5/1976 | Geddes et al. | 261/112 |
| 3,969,482 A | 7/1976 | Teller | |
| 4,008,620 A | 2/1977 | Narato et al. | 73/421.5 A |
| 4,018,388 A | 4/1977 | Andrews | |
| 4,021,021 A | 5/1977 | Hall et al. | |
| 4,127,760 A * | 11/1978 | Meyer et al. | 219/121.36 |
| 4,139,497 A | 2/1979 | Castor et al. | |
| 4,157,316 A | 6/1979 | Thompson et al. | |
| 4,171,288 A | 10/1979 | Keith et al. | |
| 4,174,298 A | 11/1979 | Antos | |
| 4,189,925 A | 2/1980 | Long | |
| 4,227,928 A | 10/1980 | Wang | |
| 4,248,387 A | 2/1981 | Andrews | |
| 4,253,917 A | 3/1981 | Wang | |
| 4,260,649 A | 4/1981 | Dension et al. | |
| 4,284,609 A | 8/1981 | deVries | |
| 4,315,874 A | 2/1982 | Ushida et al. | |
| 4,344,779 A | 8/1982 | Isserlis | |
| 4,369,167 A | 1/1983 | Weir | |
| 4,388,274 A | 6/1983 | Rourke et al. | |
| 4,419,331 A | 12/1983 | Montalvo | |
| 4,431,750 A | 2/1984 | McGinnis et al. | |
| 4,436,075 A | 3/1984 | Campbell et al. | 123/557 |
| 4,440,733 A | 4/1984 | Lawson et al. | |
| 4,458,138 A | 7/1984 | Adrian et al. | |
| 4,459,327 A | 7/1984 | Wang | |
| 4,505,945 A * | 3/1985 | Dubust et al. | 427/8 |
| 4,506,136 A * | 3/1985 | Smyth et al. | 219/121.47 |
| 4,513,149 A | 4/1985 | Gray et al. | |
| 4,523,981 A | 6/1985 | Ang et al. | |
| 4,545,872 A | 10/1985 | Sammells et al. | |
| RE32,244 E | 9/1986 | Andersen | |
| 4,609,441 A | 9/1986 | Frese, Jr. et al. | |
| 4,723,589 A | 2/1988 | Iyer et al. | |
| 4,731,517 A * | 3/1988 | Cheney | 219/121.59 |
| 4,751,021 A | 6/1988 | Mollon et al. | |
| 4,764,283 A | 8/1988 | Ashbrook et al. | |
| 4,765,805 A | 8/1988 | Wahl et al. | |
| 4,824,624 A | 4/1989 | Palicka et al. | 264/67 |
| 4,836,084 A | 6/1989 | Vogelesang et al. | |
| 4,855,505 A | 8/1989 | Koll | |
| 4,866,240 A | 9/1989 | Webber | |
| 4,885,038 A | 12/1989 | Anderson et al. | |
| 4,921,586 A | 5/1990 | Molter | |
| 4,983,555 A | 1/1991 | Roy et al. | 501/120 |
| 4,987,033 A | 1/1991 | Abkowitz et al. | 428/469 |
| 5,006,163 A | 4/1991 | Benn et al. | |
| 5,015,863 A | 5/1991 | Takeshima et al. | |
| 5,041,713 A | 8/1991 | Weidman | |
| 5,043,548 A | 8/1991 | Whitney et al. | 219/121.84 |
| 5,070,064 A | 12/1991 | Hsu et al. | |
| 5,073,193 A | 12/1991 | Chaklader et al. | 75/346 |
| 5,133,190 A | 7/1992 | Abdelmalek | |
| 5,151,296 A | 9/1992 | Tokunaga | |
| 5,157,007 A | 10/1992 | Domesle et al. | |
| 5,192,130 A | 3/1993 | Endo et al. | |
| 5,230,844 A | 7/1993 | Macaire et al. | |
| 5,233,153 A | 8/1993 | Coats | |
| 5,269,848 A | 12/1993 | Nakagawa | |
| 5,330,945 A | 7/1994 | Beckmeyer et al. | |
| 5,338,716 A | 8/1994 | Triplett et al. | |
| 5,369,241 A | 11/1994 | Taylor et al. | 219/121.47 |
| 5,371,049 A | 12/1994 | Moffett et al. | 501/89 |
| 5,372,629 A | 12/1994 | Anderson et al. | 75/332 |
| 5,392,797 A | 2/1995 | Welch | 134/108 |
| 5,436,080 A | 7/1995 | Inoue et al. | |
| 5,439,865 A | 8/1995 | Abe et al. | |
| 5,442,153 A | 8/1995 | Marantz et al. | |
| 5,460,701 A | 10/1995 | Parker et al. | |
| 5,464,458 A | 11/1995 | Yamamoto | |
| 5,485,941 A | 1/1996 | Guyomard et al. | 222/1 |
| 5,534,149 A | 7/1996 | Birkenbeil et al. | |
| 5,534,270 A | 7/1996 | De Castro | |
| 5,543,173 A | 8/1996 | Horn, Jr. et al. | |
| 5,553,507 A | 9/1996 | Basch et al. | 73/863.01 |
| 5,562,966 A | 10/1996 | Clarke et al. | |
| 5,582,807 A | 12/1996 | Liao et al. | |
| 5,611,896 A | 3/1997 | Swanepoel et al. | 204/169 |
| 5,630,322 A | 5/1997 | Heilmann et al. | 62/95 |
| 5,652,304 A | 7/1997 | Calderon et al. | |
| 5,714,644 A | 2/1998 | Irgang et al. | |
| 5,723,187 A | 3/1998 | Popoola et al. | |
| 5,726,414 A * | 3/1998 | Kitahashi et al. | 219/121.48 |
| 5,749,938 A | 5/1998 | Coombs | 75/332 |
| 5,776,359 A | 7/1998 | Schultz et al. | 252/62.51 |
| 5,788,738 A | 8/1998 | Pirzada et al. | 75/331 |
| 5,804,155 A | 9/1998 | Farrauto et al. | |
| 5,811,187 A | 9/1998 | Anderson et al. | 428/403 |
| 5,837,959 A | 11/1998 | Muehlberger et al. | |
| 5,851,507 A | 12/1998 | Pirzada et al. | |
| 5,853,815 A | 12/1998 | Muehlberger | 427/446 |
| 5,858,470 A | 1/1999 | Bernecki et al. | |
| 5,884,473 A | 3/1999 | Noda et al. | |
| 5,905,000 A | 5/1999 | Yadav et al. | 429/33 |
| 5,928,806 A | 7/1999 | Olah et al. | |
| 5,935,293 A | 8/1999 | Detering et al. | 75/10.29 |
| 5,973,289 A | 10/1999 | Read et al. | |
| 5,989,648 A | 11/1999 | Phillips | 427/456 |
| 5,993,967 A | 11/1999 | Brotzman, Jr. et al. | 428/407 |
| 5,993,988 A | 11/1999 | Ohara et al. | 429/40 |
| 6,004,620 A | 12/1999 | Camm | |
| 6,012,647 A | 1/2000 | Ruta et al. | 239/132.1 |
| 6,033,781 A | 3/2000 | Brotzman, Jr. et al. | 428/405 |
| 6,045,765 A | 4/2000 | Nakatsuji et al. | |
| 6,059,853 A | 5/2000 | Coombs | 75/332 |
| 6,066,587 A | 5/2000 | Kurokawa et al. | |
| 6,084,197 A | 7/2000 | Fusaro, Jr. | |
| 6,093,306 A | 7/2000 | Hanrahan et al. | |
| 6,093,378 A | 7/2000 | Deeba et al. | |
| 6,102,106 A | 8/2000 | Manning et al. | 165/76 |
| 6,117,376 A | 9/2000 | Merkel | |
| 6,168,694 B1 | 1/2001 | Huang et al. | |
| 6,190,627 B1 | 2/2001 | Hoke et al. | |
| 6,213,049 B1 | 4/2001 | Yang | |
| 6,214,195 B1 | 4/2001 | Yadav et al. | 205/334 |
| 6,228,904 B1 | 5/2001 | Yadav et al. | 523/210 |
| 6,254,940 B1 | 7/2001 | Pratsinis et al. | 427/562 |
| 6,261,484 B1 | 7/2001 | Phillips et al. | 264/5 |
| 6,267,864 B1 | 7/2001 | Yadav et al. | 205/341 |
| 6,322,756 B1 | 11/2001 | Arno et al. | |
| 6,342,465 B1 | 1/2002 | Klein et al. | |
| 6,344,271 B1 | 2/2002 | Yadav et al. | 428/402 |
| 6,362,449 B1 | 3/2002 | Hadidi et al. | |
| 6,379,419 B1 | 4/2002 | Celik et al. | 75/346 |
| 6,387,560 B1 | 5/2002 | Yadav et al. | 429/45 |
| 6,395,214 B1 | 5/2002 | Kear et al. | 264/434 |
| 6,398,843 B1 | 6/2002 | Tarrant | 75/249 |
| 6,409,851 B1 | 6/2002 | Sethuram et al. | 148/565 |
| 6,413,781 B1 | 7/2002 | Geis et al. | |
| 6,416,818 B1 | 7/2002 | Aikens et al. | 427/383.1 |
| RE37,853 E | 9/2002 | Detering et al. | 75/10.19 |
| 6,444,009 B1 | 9/2002 | Liu et al. | 75/332 |
| 6,475,951 B1 | 11/2002 | Domesle et al. | |
| 6,488,904 B1 | 12/2002 | Cox et al. | |
| 6,506,995 B1 | 1/2003 | Fusaro, Jr. et al. | |
| 6,517,800 B1 | 2/2003 | Cheng et al. | 423/447.1 |
| 6,524,662 B2 | 2/2003 | Jang et al. | 427/535 |
| 6,531,704 B2 | 3/2003 | Yadav et al. | 250/493.1 |
| 6,548,445 B1 | 4/2003 | Buysch et al. | |
| 6,554,609 B2 | 4/2003 | Yadav et al. | 432/9 |
| 6,562,304 B1 | 5/2003 | Mizrahi | |

(56) References Cited

U.S. PATENT DOCUMENTS

| | | | |
|---|---|---|---|
| 6,562,495 B2 | 5/2003 | Yadav et al. ............... 429/12 |
| 6,569,393 B1 | 5/2003 | Hoke et al. |
| 6,569,397 B1 | 5/2003 | Yadav et al. ............... 423/345 |
| 6,569,518 B2 | 5/2003 | Yadav et al. ............... 428/323 |
| 6,572,672 B2 | 6/2003 | Yadav et al. ............... 75/343 |
| 6,579,446 B1 | 6/2003 | Teran et al. |
| 6,596,187 B2 | 7/2003 | Coll et al. |
| 6,603,038 B1 | 8/2003 | Hagemeyer et al. |
| 6,607,821 B2 | 8/2003 | Yadav et al. ............... 428/323 |
| 6,610,355 B2 | 8/2003 | Yadav et al. ............... 427/115 |
| 6,623,559 B2 | 9/2003 | Huang |
| 6,635,357 B2 | 10/2003 | Moxson et al. ............... 428/548 |
| 6,641,775 B2 | 11/2003 | Vigliotti et al. ............... 264/618 |
| 6,652,822 B2 | 11/2003 | Phillips et al. ............... 423/290 |
| 6,652,967 B2 | 11/2003 | Yadav et al. ............... 428/403 |
| 6,669,823 B1 | 12/2003 | Sarkas et al. ............... 204/164 |
| 6,682,002 B2 | 1/2004 | Kyotani ............... 239/318 |
| 6,689,192 B1 | 2/2004 | Phillips et al. ............... 75/342 |
| 6,699,398 B1 | 3/2004 | Kim ............... 216/55 |
| 6,706,097 B2 | 3/2004 | Zomes ............... 96/153 |
| 6,706,660 B2 | 3/2004 | Park |
| 6,710,207 B2 | 3/2004 | Bogan, Jr. et al. |
| 6,713,176 B2 | 3/2004 | Yadav et al. ............... 428/402 |
| 6,716,525 B1 | 4/2004 | Yadav et al. ............... 428/402 |
| 6,744,006 B2 | 6/2004 | Johnson et al. |
| 6,746,791 B2 | 6/2004 | Yadav et al. ............... 429/30 |
| 6,772,584 B2 | 8/2004 | Chun et al. ............... 60/275 |
| 6,786,950 B2 | 9/2004 | Yadav et al. ............... 75/346 |
| 6,813,931 B2 | 11/2004 | Yadav et al. ............... 73/31.05 |
| 6,817,388 B2 | 11/2004 | Tsangaris et al. ............... 141/82 |
| 6,832,735 B2 | 12/2004 | Yadav et al. ............... 241/16 |
| 6,838,072 B1 | 1/2005 | Kong et al. ............... 423/594.2 |
| 6,841,509 B1 | 1/2005 | Hwang et al. |
| 6,855,410 B2 | 2/2005 | Buckley |
| 6,855,426 B2 | 2/2005 | Yadav ............... 428/403 |
| 6,855,749 B1 | 2/2005 | Yadav et al. ............... 523/105 |
| 6,858,170 B2 | 2/2005 | Van Thillo et al. |
| 6,886,545 B1 | 5/2005 | Holm ............... 123/568.21 |
| 6,896,958 B1 | 5/2005 | Cayton et al. ............... 428/323 |
| 6,902,699 B2 | 6/2005 | Fritzemeier et al. ............... 419/38 |
| 6,916,872 B2 | 7/2005 | Yadav et al. ............... 524/430 |
| 6,919,065 B2 | 7/2005 | Zhou et al. |
| 6,919,527 B2 | 7/2005 | Boulos et al. ............... 219/121.52 |
| 6,933,331 B2 | 8/2005 | Yadav et al. ............... 523/210 |
| 6,972,115 B1 | 12/2005 | Ballard |
| 6,986,877 B2 | 1/2006 | Takikawa et al. ............... 423/447.3 |
| 6,994,837 B2 | 2/2006 | Boulos et al. ............... 423/613 |
| 7,007,872 B2 | 3/2006 | Yadav et al. ............... 241/1 |
| 7,022,305 B2 | 4/2006 | Drumm et al. |
| 7,052,777 B2 | 5/2006 | Brotzman, Jr. et al. ............... 428/570 |
| 7,073,559 B2 | 7/2006 | O'Larey et al. ............... 164/76.1 |
| 7,081,267 B2 | 7/2006 | Yadav ............... 427/115 |
| 7,101,819 B2 | 9/2006 | Rosenflanz et al. ............... 501/10 |
| 7,147,544 B2 | 12/2006 | Rosenflanz ............... 451/28 |
| 7,147,894 B2 | 12/2006 | Zhou et al. ............... 427/256 |
| 7,166,198 B2 | 1/2007 | Van Der Walt et al. ............... 204/165 |
| 7,166,663 B2 | 1/2007 | Cayton et al. ............... 524/430 |
| 7,172,649 B2 | 2/2007 | Conrad et al. ............... 106/35 |
| 7,172,790 B2 | 2/2007 | Koulik et al. |
| 7,178,747 B2 | 2/2007 | Yadav et al. ............... 241/23 |
| 7,208,126 B2 | 4/2007 | Musick et al. ............... 423/69 |
| 7,211,236 B2 | 5/2007 | Stark et al. ............... 423/592.1 |
| 7,217,407 B2 | 5/2007 | Zhang ............... 423/610 |
| 7,220,398 B2 | 5/2007 | Sutorik et al. |
| 7,255,498 B2 | 8/2007 | Bush et al. |
| 7,265,076 B2 | 9/2007 | Taguchi et al. |
| 7,282,167 B2 | 10/2007 | Carpenter |
| 7,307,195 B2 | 12/2007 | Polverejan et al. ............... 585/443 |
| 7,323,655 B2 | 1/2008 | Kim ............... 219/121.43 |
| 7,384,447 B2 | 6/2008 | Kodas et al. ............... 75/332 |
| 7,402,899 B1 | 7/2008 | Whiting et al. |
| 7,417,008 B2 | 8/2008 | Richards et al. |
| 7,494,527 B2 | 2/2009 | Jurewicz et al. |
| 7,517,826 B2 | 4/2009 | Fujdala et al. |
| 7,534,738 B2 | 5/2009 | Fujdala et al. |
| 7,541,012 B2 | 6/2009 | Yeung et al. |
| 7,541,310 B2 | 6/2009 | Espinoza et al. |
| 7,557,324 B2 | 7/2009 | Nylen et al. |
| 7,572,315 B2 | 8/2009 | Boulos et al. |
| 7,576,029 B2 | 8/2009 | Saito et al. |
| 7,576,031 B2 | 8/2009 | Beutel et al. |
| 7,604,843 B1 | 10/2009 | Robinson et al. |
| 7,611,686 B2 | 11/2009 | Alekseeva et al. |
| 7,615,097 B2 | 11/2009 | McKechnie et al. |
| 7,618,919 B2 | 11/2009 | Shimazu et al. |
| 7,622,693 B2 | 11/2009 | Foret |
| 7,632,775 B2 | 12/2009 | Zhou et al. |
| 7,635,218 B1 | 12/2009 | Lott |
| 7,674,744 B2 | 3/2010 | Shiratori et al. |
| 7,678,419 B2 | 3/2010 | Kevwitch et al. |
| 7,704,369 B2 | 4/2010 | Olah et al. |
| 7,709,411 B2 | 5/2010 | Zhou et al. |
| 7,709,414 B2 | 5/2010 | Fujdala et al. |
| 7,745,367 B2 | 6/2010 | Fujdala et al. |
| 7,750,265 B2 | 7/2010 | Belashchenko |
| 7,803,210 B2 | 9/2010 | Sekine et al. |
| 7,851,405 B2 | 12/2010 | Wakamatsu et al. |
| 7,874,239 B2 | 1/2011 | Howland |
| 7,875,573 B2 | 1/2011 | Beutel et al. |
| 7,897,127 B2 | 3/2011 | Layman et al. |
| 7,902,104 B2 | 3/2011 | Kalck |
| 7,905,942 B1 | 3/2011 | Layman |
| 7,935,655 B2 | 5/2011 | Tolmachev |
| 8,051,724 B1 | 11/2011 | Layman et al. |
| 8,076,258 B1 | 12/2011 | Biberger |
| 8,080,494 B2 | 12/2011 | Yasuda et al. |
| 8,089,495 B2 | 1/2012 | Keller |
| 8,129,654 B2 * | 3/2012 | Lee et al. ............... 219/121.36 |
| 8,142,619 B2 | 3/2012 | Layman et al. |
| 8,168,561 B2 | 5/2012 | Virkar |
| 8,173,572 B2 | 5/2012 | Feaviour |
| 8,211,392 B2 | 7/2012 | Grubert et al. |
| 8,258,070 B2 | 9/2012 | Fujdala et al. |
| 8,278,240 B2 | 10/2012 | Tange et al. |
| 8,294,060 B2 | 10/2012 | Mohanty et al. |
| 8,309,489 B2 | 11/2012 | Cuenya et al. |
| 8,349,761 B2 | 1/2013 | Xia et al. |
| 8,557,727 B2 | 10/2013 | Yin et al. |
| 2001/0004009 A1 | 6/2001 | MacKelvie |
| 2001/0042802 A1 | 11/2001 | Youds |
| 2001/0055554 A1 | 12/2001 | Hoke et al. |
| 2002/0018815 A1 | 2/2002 | Sievers et al. |
| 2002/0068026 A1 | 6/2002 | Murrell et al. |
| 2002/0071800 A1 | 6/2002 | Hoke et al. |
| 2002/0079620 A1 | 6/2002 | DuBuis et al. ............... 264/328.14 |
| 2002/0100751 A1 | 8/2002 | Carr |
| 2002/0102674 A1 | 8/2002 | Anderson |
| 2002/0131914 A1 | 9/2002 | Sung |
| 2002/0143417 A1 | 10/2002 | Ito et al. |
| 2002/0182735 A1 | 12/2002 | Kibby et al. |
| 2002/0183191 A1 | 12/2002 | Faber et al. |
| 2002/0192129 A1 | 12/2002 | Shamouilian et al. |
| 2003/0036786 A1 | 2/2003 | Duren et al. ............... 607/96 |
| 2003/0042232 A1 | 3/2003 | Shimazu |
| 2003/0047617 A1 | 3/2003 | Shanmugham et al. |
| 2003/0066800 A1 | 4/2003 | Saim et al. |
| 2003/0108459 A1 | 6/2003 | Wu et al. ............... 422/186.04 |
| 2003/0110931 A1 | 6/2003 | Aghajanian et al. |
| 2003/0129098 A1 | 7/2003 | Endo et al. |
| 2003/0139288 A1 | 7/2003 | Cai et al. |
| 2003/0143153 A1 | 7/2003 | Boulos et al. |
| 2003/0172772 A1 | 9/2003 | Sethuram et al. |
| 2003/0223546 A1 | 12/2003 | McGregor et al. ............... 378/143 |
| 2004/0009118 A1 | 1/2004 | Phillips et al. |
| 2004/0023302 A1 | 2/2004 | Archibald et al. |
| 2004/0023453 A1 | 2/2004 | Xu et al. |
| 2004/0077494 A1 | 4/2004 | LaBarge et al. |
| 2004/0103751 A1 | 6/2004 | Joseph et al. ............... 75/10.19 |
| 2004/0109523 A1 | 6/2004 | Singh et al. |
| 2004/0119064 A1 | 6/2004 | Narayan et al. |
| 2004/0127586 A1 | 7/2004 | Jin et al. |
| 2004/0166036 A1 | 8/2004 | Chen et al. |
| 2004/0167009 A1 | 8/2004 | Kuntz et al. ............... 501/95.2 |
| 2004/0176246 A1 | 9/2004 | Shirk et al. |

(56) References Cited

U.S. PATENT DOCUMENTS

| | | |
|---|---|---|
| 2004/0208805 A1 | 10/2004 | Fincke et al. |
| 2004/0213998 A1 | 10/2004 | Hearley et al. |
| 2004/0238345 A1 | 12/2004 | Koulik et al. |
| 2004/0251017 A1 | 12/2004 | Pillion et al. ............... 165/289 |
| 2004/0251241 A1 | 12/2004 | Blutke et al. |
| 2005/0000321 A1 | 1/2005 | O'Larey et al. ............... 75/952 |
| 2005/0000950 A1 | 1/2005 | Schroder et al. ......... 219/121.59 |
| 2005/0066805 A1 | 3/2005 | Park et al. |
| 2005/0070431 A1 | 3/2005 | Alvin et al. |
| 2005/0077034 A1 | 4/2005 | King ............... 165/163 |
| 2005/0097988 A1 | 5/2005 | Kodas et al. ............... 75/332 |
| 2005/0106865 A1 | 5/2005 | Chung et al. |
| 2005/0133121 A1 | 6/2005 | Subramanian et al. |
| 2005/0163673 A1 | 7/2005 | Johnson et al. |
| 2005/0199739 A1 | 9/2005 | Kuroda et al. |
| 2005/0220695 A1 | 10/2005 | Abatzoglou et al. |
| 2005/0227864 A1 | 10/2005 | Sutorik et al. |
| 2005/0233380 A1 | 10/2005 | Pesiri et al. ............... 435/7.1 |
| 2005/0240069 A1 | 10/2005 | Polverejan et al. ........... 585/444 |
| 2005/0258766 A1 | 11/2005 | Kim ............... 315/111.21 |
| 2005/0275143 A1 | 12/2005 | Toth |
| 2006/0051505 A1 | 3/2006 | Kortshagen et al. .......... 427/212 |
| 2006/0068989 A1 | 3/2006 | Ninomiya et al. |
| 2006/0094595 A1 | 5/2006 | Labarge |
| 2006/0096393 A1 | 5/2006 | Pesiri ............... 73/863.21 |
| 2006/0105910 A1 | 5/2006 | Zhou et al. |
| 2006/0108332 A1 | 5/2006 | Belashchenko .......... 219/121.47 |
| 2006/0153728 A1 | 7/2006 | Schoenung et al. |
| 2006/0153765 A1 | 7/2006 | Pham-Huu et al. |
| 2006/0159596 A1 | 7/2006 | De La Veaux et al. ........ 422/151 |
| 2006/0166809 A1 | 7/2006 | Malek et al. |
| 2006/0211569 A1 | 9/2006 | Dang et al. |
| 2006/0213326 A1 | 9/2006 | Gollob et al. |
| 2006/0222780 A1 | 10/2006 | Gurevich et al. |
| 2006/0231525 A1 | 10/2006 | Asakawa et al. ............... 216/56 |
| 2007/0048206 A1 | 3/2007 | Hung et al. |
| 2007/0049484 A1 | 3/2007 | Kear et al. |
| 2007/0063364 A1 | 3/2007 | Hsiao et al. ............... 264/5 |
| 2007/0084308 A1 | 4/2007 | Nakamura et al. ............... 75/346 |
| 2007/0084834 A1 | 4/2007 | Hanus et al. ............... 219/121.5 |
| 2007/0087934 A1 | 4/2007 | Martens et al. ............... 502/214 |
| 2007/0163385 A1 | 7/2007 | Takahashi et al. |
| 2007/0173403 A1 | 7/2007 | Koike et al. |
| 2007/0178673 A1 | 8/2007 | Gole et al. |
| 2007/0221404 A1 | 9/2007 | Das et al. |
| 2007/0253874 A1 | 11/2007 | Foret |
| 2007/0292321 A1 | 12/2007 | Plischke et al. |
| 2008/0006954 A1 | 1/2008 | Yubuta et al. |
| 2008/0026041 A1 | 1/2008 | Tepper et al. |
| 2008/0031806 A1 | 2/2008 | Gavenonis et al. |
| 2008/0038578 A1 | 2/2008 | Li |
| 2008/0045405 A1 | 2/2008 | Beutel et al. |
| 2008/0047261 A1 | 2/2008 | Han et al. |
| 2008/0057212 A1 | 3/2008 | Dorier et al. |
| 2008/0064769 A1 | 3/2008 | Sato et al. |
| 2008/0104735 A1 | 5/2008 | Howland |
| 2008/0105083 A1 | 5/2008 | Nakamura et al. |
| 2008/0116178 A1 | 5/2008 | Weidman |
| 2008/0125308 A1 | 5/2008 | Fujdala et al. |
| 2008/0125313 A1 | 5/2008 | Fujdala et al. |
| 2008/0138651 A1 | 6/2008 | Doi et al. |
| 2008/0175936 A1 | 7/2008 | Tokita et al. |
| 2008/0187714 A1 | 8/2008 | Wakamatsu et al. |
| 2008/0206562 A1 | 8/2008 | Stucky et al. |
| 2008/0207858 A1 | 8/2008 | Kowaleski et al. |
| 2008/0248704 A1 | 10/2008 | Mathis et al. |
| 2008/0274344 A1 | 11/2008 | Vieth et al. |
| 2008/0277092 A1 | 11/2008 | Layman et al. |
| 2008/0277266 A1 | 11/2008 | Layman |
| 2008/0277267 A1 | 11/2008 | Biberger et al. |
| 2008/0277268 A1 | 11/2008 | Layman |
| 2008/0277269 A1 | 11/2008 | Layman et al. |
| 2008/0277270 A1 | 11/2008 | Biberger et al. |
| 2008/0277271 A1 | 11/2008 | Layman |
| 2008/0280049 A1 | 11/2008 | Kevwitch et al. |
| 2008/0280751 A1 | 11/2008 | Harutyunyan et al. |
| 2008/0280756 A1 | 11/2008 | Biberger |
| 2008/0283411 A1 | 11/2008 | Eastman et al. |
| 2008/0283498 A1 | 11/2008 | Yamazaki |
| 2009/0010801 A1 | 1/2009 | Murphy et al. |
| 2009/0054230 A1 | 2/2009 | Veeraraghavan et al. |
| 2009/0088585 A1 | 4/2009 | Schammel et al. |
| 2009/0092887 A1 | 4/2009 | McGrath et al. |
| 2009/0098402 A1 | 4/2009 | Kang et al. |
| 2009/0114568 A1 | 5/2009 | Trevino et al. |
| 2009/0162991 A1 | 6/2009 | Beneyton et al. |
| 2009/0168506 A1 | 7/2009 | Han et al. |
| 2009/0170242 A1 | 7/2009 | Lin et al. |
| 2009/0181474 A1 | 7/2009 | Nagai |
| 2009/0200180 A1 | 8/2009 | Capote et al. |
| 2009/0208367 A1 | 8/2009 | Calio et al. |
| 2009/0209408 A1 | 8/2009 | Kitamura et al. |
| 2009/0223410 A1 | 9/2009 | Jun et al. |
| 2009/0253037 A1 | 10/2009 | Park et al. |
| 2009/0274903 A1 | 11/2009 | Addiego |
| 2009/0286899 A1 | 11/2009 | Hofmann et al. |
| 2009/0324468 A1 | 12/2009 | Golden et al. |
| 2010/0089002 A1 | 4/2010 | Merkel |
| 2010/0092358 A1 | 4/2010 | Koegel et al. |
| 2010/0124514 A1 | 5/2010 | Chelluri et al. |
| 2010/0166629 A1 | 7/2010 | Deeba |
| 2010/0180581 A1 | 7/2010 | Grubert et al. |
| 2010/0180582 A1 | 7/2010 | Mueller-Stach et al. |
| 2010/0186375 A1 | 7/2010 | Kazi et al. |
| 2010/0240525 A1 | 9/2010 | Golden et al. |
| 2010/0275781 A1 | 11/2010 | Tsangaris |
| 2011/0006463 A1 | 1/2011 | Layman |
| 2011/0052467 A1 | 3/2011 | Chase et al. |
| 2011/0143041 A1 | 6/2011 | Layman et al. |
| 2011/0143915 A1 | 6/2011 | Yin et al. |
| 2011/0143916 A1 | 6/2011 | Leamon |
| 2011/0143930 A1 | 6/2011 | Yin et al. |
| 2011/0143933 A1 | 6/2011 | Yin et al. |
| 2011/0144382 A1 | 6/2011 | Yin et al. |
| 2011/0152550 A1 | 6/2011 | Grey et al. |
| 2011/0158871 A1 | 6/2011 | Arnold et al. |
| 2011/0174604 A1 | 7/2011 | Duesel et al. |
| 2011/0243808 A1 | 10/2011 | Fossey et al. |
| 2011/0245073 A1 | 10/2011 | Oljaca et al. |
| 2011/0247336 A9 | 10/2011 | Farsad et al. |
| 2011/0305612 A1 | 12/2011 | Müller-Stach et al. |
| 2012/0023909 A1 | 2/2012 | Lambert et al. |
| 2012/0045373 A1 | 2/2012 | Biberger |
| 2012/0097033 A1 | 4/2012 | Arnold et al. |
| 2012/0122660 A1 | 5/2012 | Andersen et al. |
| 2012/0124974 A1 | 5/2012 | Li et al. |
| 2012/0171098 A1 | 7/2012 | Hung et al. |
| 2012/0308467 A1 | 12/2012 | Carpenter et al. |
| 2013/0213018 A1 | 8/2013 | Yin et al. |

FOREIGN PATENT DOCUMENTS

| | | | |
|---|---|---|---|
| GB | 1 307 941 A | 2/1973 | |
| JP | 56-146804 | 11/1981 | ............... B22F 9/08 |
| JP | 61-086815 A | 5/1986 | |
| JP | 62-102827 A | 5/1987 | |
| JP | 63-214342 A | 9/1988 | |
| JP | 1-164795 A | 6/1989 | |
| JP | 05-228361 A | 9/1993 | |
| JP | 05-324094 A | 12/1993 | |
| JP | 6-93309 A | 4/1994 | |
| JP | 6-135797 A | 5/1994 | |
| JP | 6-272012 A | 9/1994 | |
| JP | H06-065772 | 9/1994 | |
| JP | 7031873 A | 2/1995 | |
| JP | 07-256116 A | 10/1995 | |
| JP | 8-158033 A | 6/1996 | |
| JP | 10-130810 A | 5/1998 | |
| JP | 11-502760 A | 3/1999 | |
| JP | 2000-220978 A | 8/2000 | |
| JP | 2002-88486 A | 3/2002 | |
| JP | 2002-336688 A | 11/2002 | |
| JP | 2004-233007 A | 8/2004 | |
| JP | 2004-249206 A | 9/2004 | |

(56) References Cited

FOREIGN PATENT DOCUMENTS

| | | | |
|---|---|---|---|
| JP | 2004-290730 A | 10/2004 | |
| JP | 2005-503250 A | 2/2005 | |
| JP | 2005-122621 A | 5/2005 | |
| JP | 2005-218937 A | 8/2005 | |
| JP | 2005-342615 A | 12/2005 | |
| JP | 2006-001779 A | 1/2006 | |
| JP | 2006-508885 A | 3/2006 | |
| JP | 2006-247446 A | 9/2006 | |
| JP | 2006-260385 A | 9/2006 | |
| JP | 2007-46162 A | 2/2007 | |
| JP | 2007-203129 A | 8/2007 | |
| SU | 493241 | 3/1976 | |
| TW | 200611449 | 4/2006 | |
| TW | 201023207 | 6/2010 | |
| WO | WO-96/28577 A1 | 9/1996 | |
| WO | WO 02/092503 A1 | 11/2002 | C01B 21/064 |
| WO | 2004052778 A2 | 6/2004 | |
| WO | WO-2005/063390 A1 | 7/2005 | |
| WO | WO 2006/079213 A1 | 8/2006 | B01J 2/04 |
| WO | WO-2008/130451 A2 | 10/2008 | |
| WO | WO-2008/130451 A3 | 10/2008 | |
| WO | WO-2011/081833 A1 | 7/2011 | |

OTHER PUBLICATIONS

Kenvin et al. "Supported Catalysts Prepared from Monouclear Copper Complexes: Catalytic Properties", Journal of Catalysis, pp. 81-91.
National Aeronautics and Space Administration, "Enthalpy", http://www.grc.nasa.gov/WWW/K-12/airplane/enthalpy.html, Nov. 23, 2009, 1 page.
Han et al., Deformation Mechanisms and Ductility of Nanostructured Al Alloys, Mat. Res. Soc. Symp. Proc. vol. 821, Jan. 2004, Material Research Society, http://www.mrs.org/s_mrs/bin.asp?CID=2670&DOC=FILE.PDF., 6 pages.
United States Patent and Trademark Office, Office Action, mailed Feb. 19, 2010, U.S. Appl. No. 12/152,109, filed May 9, 2008, First Named Inventor: Maximilian A. Biberger, 17 pages.
Derwent English Abstract for publication No. SU 193241 A, Application No. 1973SU1943286 filed on Jul. 2, 1973, published on Mar. 1, 1976, entitled"Catalyst for Ammonia Synthesis Contains Oxides of Aluminium, Potassium, Calcium, Iron and Nickel Oxide for Increased Activity," 3 pgs.
J. Heberlein, "New Approaches in Thermal Plasma Technology", Pure Appl. Chem., vol. 74, No. 3, 2002, pp. 327-335.
T. Yoshida, "The Future of Thermal Plasma Processing for Coating", Pure & Appl. Chem., vol. 66, No. 6, 1994 pp. 1223-1230.
A. Gutsch et al., "Gas-Phase Production of Nanoparticles", Kona No. 20, 2002, pp. 24-37.
Dr. Heike Mühlenweg et al., "Gas-Phase Reactions—Open Up New Roads to Nanoproducts", Degussa ScienceNewsletter No. 08, 2004, pp. 12-16.
Coating Generation: Vaporization of Particles in Plasma Spraying and Splat Formation, M. Vardelle, A. Vardelle, K-I li, P. Fauchais, Universite de Limoges, 123 Avenue A. Thomas 87000, Limoges, F. , Pure & Chem, vol. 68, No. 5, pp. 1093-1099, 1996.
H. Konrad et al., "Nanostructured Cu-Bi Alloys Prepared by Co-Evaporation in a Continuous Gas Flow," NanoStructured Materials, vol. 7, No. 6, Apr. 1996, pp. 605-610.
M.Vardelle et al., "Experimental Investigation of Powder Vaporization in Thermal Plasma Jets," Plasma Chemistry and Plasma Processing, vol. 11, No. 2, Jun. 1991, pp. 185-201.
P. Fauchais et al., "Plasma Spray: Study of the Coating Generation," Ceramics International, Elsevier, Amsterdam, NL, vol. 22, No. 4, Jan. 1996, pp. 295-303.
P. Fauchais et al., "Les Dépôts Par Plasma Thermique," Revue Generale De L'Electricitie, RGE. Paris, FR, No. 2, Jan. 1993, pp. 7-12.
P. Fauchais et al, "La Projection Par Plasma: Une Revue," Annales De Physique, vol. 14, No. 3, Jun. 1989, pp. 261-310.

Stiles, A. B. (Jan. 1, 1987). "Manufacture of Carbon-Supported Metal Catalysts," in Catalyst Supports and Supported Catalysts, Butterworth Publishers, MA, pp. 125-132.
Bateman, J. E. et al. (Dec. 17, 1998). "Alkylation of Porous Silicon by Direct Reaction with Alkenes and Alkynes," Angew. Chem Int. Ed. 37(19):2683-2685.
Carrot, G. et al. (Sep. 17, 2002). "Surface-Initiated Ring-Opening Polymerization: A Versatile Method for Nanoparticle Ordering," Macromolecules 35(22):8400-8404.
Chen, H.-S. et al. (Jul. 3, 2001). "On the Photoluminescence of Si Nanoparticles," Mater. Phys. Mech. 4:62-66.
Fojtik, A. et al. (Apr. 29, 1994). "Luminescent Colloidal Silicon Particles,"Chemical Physics Letters 221 :363-367.
Fojtik, A. (Jan. 13, 2006). "Surface Chemistry of Luminescent Colloidal Silicon Nanoparticles," J. Phys. Chem. B. 110(5):1994-1998.
Hua, F. et al. (Mar. 2006). "Organically Capped Silicon Nanoparticles With Blue Photoluminescence Prepared by Hydrosilylation Followed by Oxidation," Langmuir 22(9):4363-4370.
Jouet, R. J. et al. (Jan. 25, 2005). "Surface Passivation of Bare Aluminum Nanoparticles Using Perfluoroalkyl Carboxylic Acids," Chem. Mater.17(11):2987-2996.
Kim, N. Y. et al. (Mar. 5, 1997). "Thermal Derivatization of Porous Silicon with Alcohols," J. Am. Chem. Soc. 119(9):2297-2298.
Kwon, Y.-S. et al. (Apr. 30, 2003). "Passivation Process for Superfine Aluminum Powders Obtained by Electrical Explosion of Wires," Applied Surface Science 211:57-67.
Langner, A. et al. (Aug. 25, 2005). "Controlled Silicon Surface Functionalization by Alkene Hydrosilylation," J. Am. Chem. Soc. 127(37):12798-12799.
Li, D. et al. (Apr. 9, 2005). "Environmentally Responsive "Hairy" Nanoparticles: Mixed Homopolymer Brushes on Silica Nanoparticles Synthesized by Living Radical Polymerization Techniques," J. Am. Chem. Soc. 127(7):6248-6256.
Li, X. et al. (May 25, 2004). "Surface Functionalization of Silicon Nanoparticles Produced by Laser-Driven Pyrolysis of Silane Followed by $HF-HNO_3$ Etching," Langmuir 20(11):4720-4727.
Liao, Y.-C. et al. (Jun. 27, 2006). "Self-Assembly of Organic Monolayers on Aerosolized Silicon Nanoparticles," J.Am. Chem. Soc. 128(28):9061-9065.
Liu, S.-M. et al. (Jan. 13, 2006). "Enhanced Photoluminescence from Si Nano-Organosols by Functionalization With Alkenes and Their Size Evolution," Chem. Mater. 18(3):637-642.
Neiner, D. (Aug. 5, 2006). "Low-Temperature Solution Route to Macroscopic Amounts of Hydrogen Terminated Silicon Nanoparticles," J. Am. Chem. Soc. 128:11016-11017.
Netzer, L. et al. (1983). "A New Approach to Construction of Artificial Monolayer Assemblies," J. Am. Chem. Soc. 105(3):674-676.
Sailor, M. J. (1997). "Surface Chemistry of Luminescent Silicon Nanocrystallites," Adv. Mater. 9(10):783-793.
Tao, Y.-T. (May 1993). "Structural Comparison of Self-Assembled Monolayers of n-Alkanoic Acids on the surfaces of Silver, Copper, and Aluminum," J. Am. Chem. Soc. 115(10):4350-4358.
Zou, J. et al. (Jun. 4, 2004). "Solution Synthesis of Ultrastable Luminescent Siloxane-Coated Silicon Nanoparticles," Nano Letters 4(7):1181-1186.
U.S. Appl. No. 12/001,602, filed Dec. 11, 2007, for Biberger et al.
U.S. Appl. No. 12/001,643, filed Dec. 11, 2007, for Biberger et al.
U.S. Appl. No. 12/001,644, filed Dec. 11, 2007, for Biberger et al.
U.S. Appl. No. 12/152,084, filed May 9, 2008, for Biberger.
U.S. Appl. No. 12/152,111, filed May 9, 2008, for Biberger et al.
U.S. Appl. No. 12/474,081, filed May 28, 2009, for Biberger et al.
U.S. Appl. No. 12/943,909, filed Nov. 10, 2010, for Layman.
U.S. Appl. No. 12/954,813, filed Nov. 26, 2010, for Biberger.
U.S. Appl. No. 12/954,822, filed Nov. 26, 2010, for Biberger.
U.S. Appl. No. 12/961,030, filed Dec. 6, 2010, for Lehman.
U.S. Appl. No. 12/961,108, filed Dec. 6, 2010, for Lehman.
U.S. Appl. No. 12/961,200, filed Dec. 6, 2010, for Lehman.
U.S. Appl. No. 12/962,463, filed Dec. 7, 2010, for Leamon.
U.S. Appl. No. 12/962,523, filed Dec. 7, 2010, for Yin et al.
U.S. Appl. No. 12/962,533, filed Dec. 7, 2010, for Yin et al.
U.S. Appl. No. 12/968,235, filed Dec. 14, 2010, for Biberger.
U.S. Appl. No. 12/968,239, filed Dec. 14, 2010, for Biberger.

(56) References Cited

OTHER PUBLICATIONS

U.S. Appl. No. 12/968,241, filed Dec. 14, 2010, for Biberger.
U.S. Appl. No. 12/968,245, filed Dec. 14, 2010, for Biberger.
U.S. Appl. No. 12/968,248, filed Dec. 14, 2010, for Biberger.
U.S. Appl. No. 12/968,253, filed Dec. 14, 2010, for Biberger.
U.S. Appl. No. 12/969,087, filed Dec. 15, 2010, for Biberger.
U.S. Appl. No. 12/969,128, filed Dec. 15, 2010, for Biberger.
U.S. Appl. No. 12/969,306, filed Dec. 15, 2010, for Lehman et al.
U.S. Appl. No. 12/969,447, filed Dec. 15, 2010, for Biberger et al.
U.S. Appl. No. 12/969,457, filed Nov. 15, 2010, for Leamon et al.
U.S. Appl. No. 12/969,503, filed Nov. 15, 2010, for Leamon et al.
U.S. Appl. No. 13/028,693, filed Feb. 16, 2011, for Biberger.
U.S. Appl. No. 13/033,514, filed Feb. 23, 2011, for Biberger et al.
U.S. Appl. No. 13/291,983, filed Nov. 8, 2011, for Layman et al.
Babin, A. et al. (1985). "Solvents Used in the Arts," *Center for Safety in the Arts*: 16 pages.
Chen, W.-J. et al. (Mar. 18, 2008). "Functional $Fe_3O_4/TiO_2$ Core/Shell Magnetic Nanoparticles as Photokilling Agents for Pathogenic Bacteria," *Small* 4(4): 485-491.
Faber, K. T. et al. (Sep. 1988). "Toughening by Stress-Induced Microcracking in Two-Phase Ceramics," *Journal of the American Ceramic Society* 71: C-399-C401.
Gangeri, M. et al. (2009). "Fe and Pt Carbon Nanotubes for the Electrocatalytic Conversion of Carbon Dioxide to Oxygenates," *Catalysis Today* 143: 57-63.
Ji, Y. et al. (Nov. 2002) "Processing and Mechanical Properties of $Al_2O_3$-5 vol. % Cr Nanocomposites," *Journal of the European Ceramic Society* 22(12):1927-1936.

Luo, J. et al. (2008). "Core/Shell Nanoparticles as Electrocatalysts for Fuel Cell Reactions," *Advanced Materials* 20: 4342-4347.
Mignard, D. et al. (2003). "Methanol Synthesis from Flue-Gas $CO_2$ and Renewable Electricity: A Feasibility Study," *International Journal of Hydrogen Energy* 28: 455-464.
Park, H.-Y. et al. (May 30, 2007). "Fabrication of Magnetic Core@Shell Fe Oxide@Au Nanoparticles for Interfacial Bioactivity and Bio-Separation," *Langmuir* 23: 9050-9056.
Park, N.-G. et al. (Feb. 17, 2004). "Morphological and Photoelectrochemical Characterization of Core-Shell Nanoparticle Films for Dye-Sensitized Solar Cells: Zn-O Type Shell on $SnO_2$ and $TiO_2$ Cores," *Langmuir* 20: 4246-4253.
"Plasma Spray and Wire Flame Spray Product Group," located at http://www.processmaterials.com/spray.html, published by Process Materials, Inc., last accessed Aug. 5, 2013, 2 pages.
"Platinum Group Metals: Annual Review 1996" (Oct. 1997). Engineering and Mining Journal, p. 63.
Rahaman, R. A. et al. (1995). "Synthesis of Powders," in *Ceramic Processing and Sintering*. Marcel Decker, Inc., New York, pp. 71-77.
Subramanian, S. et al. (1991). "Structure and Activity of Composite Oxide Supported Platinum-Iridium Catalysts," *Applied Catalysts* 74: 65-81.
Ünal, N. et al. (Nov. 2011). "Influence of WC Particles on the Microstructural and Mechanical Properties of 3 mol% $Y_2O_3$ Stabilized $ZrO_2$ Matrix Composites Produced by Hot Pressing," Journal of the European Ceramic Society (31)13: 2267-2275.
U.S. Appl. No. 13/589,024, filed Aug. 17, 2012, for Yin et al.
U.S. Appl. No. 13/801,726, filed Mar. 13, 2013, for Qi et al.

\* cited by examiner

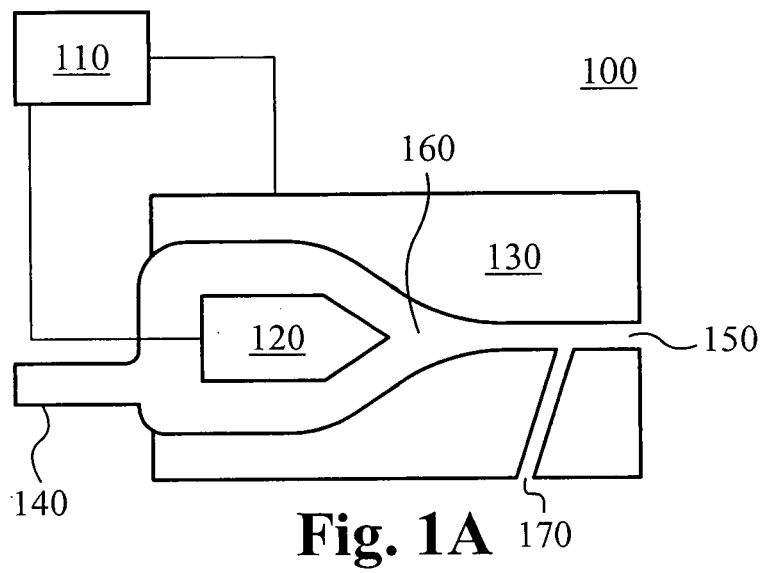
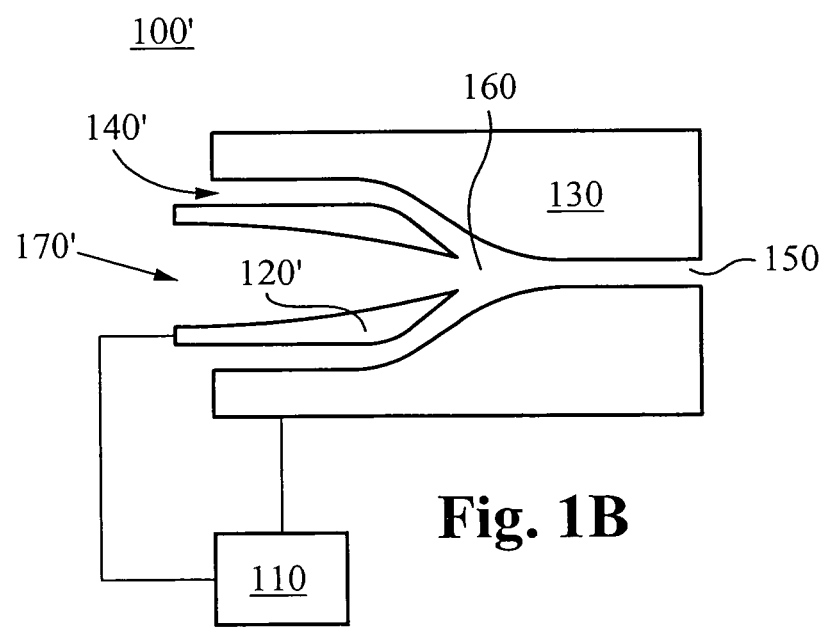

PLASMA-ARC VAPORIZATION CHAMBER WITH WIDE BORE

CROSS-REFERENCE TO RELATED APPLICATIONS

The present application claims priority to U.S. Provisional Application Ser. No. 60/928,946, filed May 11, 2007, entitled "MATERIAL PRODUCTION SYSTEM AND METHOD," which is hereby incorporated by reference as if set forth herein. The co-pending U.S. patent application Ser. No. 11/110,341, filed on Apr. 10, 2005, entitled, "HIGH THROUGHPUT DISCOVERY OF MATERIALS THROUGH VAPOR PHASE SYNTHESIS" is incorporated by reference.

FIELD OF THE INVENTION

The present invention relates to systems for and methods of vaporizing materials within a plasma-arc device. More particularly, the present invention relates to systems configured to achieve full vaporization of powders within a plasma-arc device.

BACKGROUND OF THE INVENTION

There are a great many devices adapted for thermal spraying using a plasma arc gun. For an example, see U.S. Pat. No. 6,897,402 to Crawmer.

Typically, these devices use a cathode and anode combination that defines a chamber through which gas is flowed. During operation, electricity is passed between the cathode and the anode, forming an arc that energizes the gas to form plasma. A continuous stream of gas is supplied to the gun, formed into plasma, and then ejected from the plasma gun.

When used for coating, these devices are adapted with a port configured to deposit powder into the stream of plasma prior to ejection from the gun. As powder material is deposited, the powder grains partially melt. The stream of plasma and melting particles is directed from the gun through an atmosphere where it cools slightly, and onto a surface where it sticks and hardens to form a coating.

At typical energies, full melting and vaporization of the coating material does not occur prior to ejection. Unfortunately, some applications, such as powder production (as opposed to coating), require full vaporization to achieve desired purities or small grain sizes. A naive route to achieve full vaporization dictates simply running a plasma-arc gun, such as a Crawmer-like device, at higher power. However, because the vaporization points of the materials used in powder production applications are often very high, the power necessary to achieve full vaporization of commercially available powders would destroy the device.

What is needed in the art is a system for and method of achieving full vaporization of powders, while minimizing the wear on the plasma-arc gun.

SUMMARY OF THE INVENTION

The disclosure provides exemplary embodiments of the present invention. In general, the embodiments of the present invention presented relate to long-lasting plasma-arc vaporization chambers configured to operate at high power and mass flow rates.

In one aspect of the present invention, a vaporization chamber is provided. The vaporization chamber comprises a male electrode and a female electrode. The female electrode comprises a first material and has a first end, a second end opposite the first end, and an internal chamber formed within the female electrode in between the first end and the second end. The internal chamber comprises an entry region, a frusto-conical region, and an isthmus region. The entry region is disposed at the first end and configured to receive a working gas. The frusto-conical region extends from the entry region to the isthmus region. The isthmus region has a diameter of at least 0.400 of an inch and extends to the second end along a longitudinal axis of the female electrode. The second end forms a mouth through which a fluid can exit the internal chamber along the longitudinal axis. A vortexing gas injector is disposed proximate the first end and fluidly coupled to the entry region of the internal chamber. The vortexing gas injector is configured to receive a working gas, to produce a vortexing stream of the working gas, and to supply the vortexing stream of working gas to the frusto-conical region of the internal chamber. An electrical connection point is disposed on at least one of the male electrode and the female electrode. The electrical connection point is configured to deliver energy to the vortexing stream of working gas in the frusto-conical region upon receiving power from a power supply, thereby producing an arc between the male electrode and the female electrode within the frusto-conical region of the internal chamber and producing a vortexing stream of plasma that flows into the isthmus region. The vaporization chamber further comprises a target region configured to act as lining for the female electrode in at least a portion of the frusto-conical region and in at least a portion of the isthmus region of the internal chamber. The target region comprises a second material that is distinct from the first material and that is conductive. Furthermore, the target region is configured to protect at least a portion of the female electrode from direct contact with the arc. The vaporization chamber also includes a material delivery port configured to deliver powder into the isthmus region of the internal chamber at an angle counter to the flow of the vortexing stream of plasma, and a mouth flange cooling chamber disposed at the second end of the female electrode adjacent to the mouth. The mouth flange cooling chamber is configured to permit circulation of cooling fluid around the longitudinal axis, thereby cooling the mouth when plasma exits the internal chamber.

In another aspect of the present invention, a method for vaporizing powder is provided. The method comprises providing a vaporization chamber having a male electrode and a female electrode. The female electrode is formed from a first material and has a first end, a second end opposite the first end, and an internal chamber formed within the female electrode in between the first end and the second end. The internal chamber comprises an entry region, a frusto-conical region, and an isthmus region. The entry region is disposed at the first end and is configured to receive a working gas. The frusto-conical region extends from the entry region to the isthmus region. The isthmus region has a diameter of at least 0.400 of an inch and extends to the second end along a longitudinal axis of the female electrode. The second end forms a mouth through which a fluid can exit the internal chamber along the longitudinal axis. The method further comprises flowing a working gas into the internal chamber through a vortexing gas injector disposed at the entry region, thereby producing a vortexing stream of working gas. The vortexing stream of working gas flows into the frusto-conical region. Energy is delivered to the vortexing stream of working gas in the frusto-conical region, thereby producing an arc between the male electrode and the female electrode and producing a vortexing stream of plasma. The arc directly contacts a conductive target region. The target region comprises a second material that is distinct from the first material. The target region protects at least a portion of the female electrode from direct contact with the arc. The vortexing stream of plasma flows through the isthmus region, which has a diameter of at least 0.400 of an inch. A powder is injected through the female electrode into the isthmus region at an angle counter to the flow of the vortexing stream of plasma. The powder and the vortexing stream of plasma are mixed. The plasma vaporizes the powder, thereby forming a fluid stream comprising the vaporized powder. Finally, the fluid stream is ejected out of the internal chamber through a mouth disposed at the second end of the female electrode. The mouth is cooled by a flange cooling member disposed adjacent to the mouth. The flange cooling member comprises a mouth flange cooling chamber configured to permit circulation of cooling fluid around the longitudinal axis of the female electrode.

In preferred embodiments, a housing supports the positioning of the male electrode and the female electrode.

Additionally, the mouth flange cooling chamber can be brazed onto the second end of the female electrode.

Furthermore, the vaporization chamber can also include a network of coolant channels disposed within the housing. This network of coolant channels is configured to permit circulation of coolant around the female electrode and into the mouth flange cooling chamber.

In a preferred embodiment, the isthmus region of the internal chamber has a maximum diameter of 0.500 of an inch.

Additionally, the target region preferably comprises tungsten

Furthermore, the material delivery port is preferably configured to deliver the powder into the isthmus region of the internal chamber at an angle pitched at least 20 degrees towards the entry region measured from a plane perpendicular to the flow of the vortexing stream of plasma.

In a preferred embodiment, the vaporization chamber further comprises a gas supply system fluidly coupled to the vortexing gas injector. The gas supply system is configured to supply the working gas to the vortexing gas injector. The working gas preferably comprises hydrogen and an inert gas, such as argon.

In a preferred embodiment, the vaporization chamber further comprises a power supply that is connected to the electrical connection point. The power supply is preferably configured to produce a vortexing stream of plasma having an electric current greater than 1000 amperes. Additionally, the gas supply system is preferably configured to supply the working gas at a flow rate greater than 5 liters per minute.

BRIEF DESCRIPTION OF THE DRAWINGS

FIG. 1A is a cross-sectional schematic illustration of one embodiment of a plasma gun including a powder port in the female electrode.

FIG. 1B is a cross-sectional schematic illustration of one embodiment of a plasma gun with a powder port in the male electrode.

DETAILED DESCRIPTION OF THE INVENTION

Figure 1C:
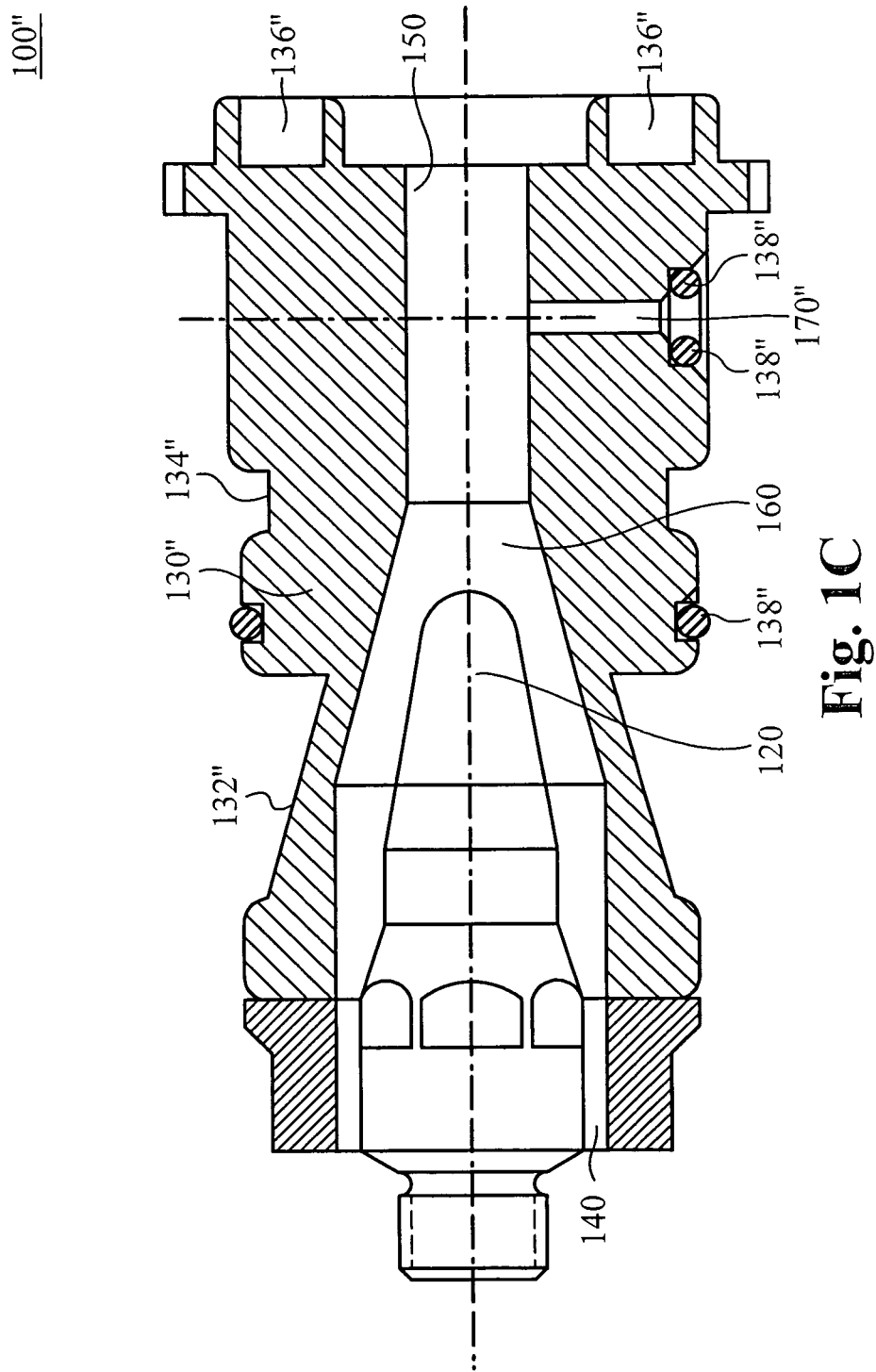
FIG. 1C is a cross-sectional schematic illustration of one embodiment of a plasma gun including a powder port in a female anode adapted for liquid cooling.

The description below concerns several embodiments of the invention. The discussion references the illustrated preferred embodiment. However, the scope of the present invention is not limited to either the illustrated embodiment, nor is it limited to those discussed. To the contrary, the scope should be interpreted as broadly as possible based on the language of the Claims section of this document.

In the following description, numerous details and alternatives are set forth for purpose of explanation. However, one of ordinary skill in the art will realize that the invention can be practiced without the use of these specific details. In other instances, well-known structures and devices are shown in block diagram form in order not to obscure the description of the invention with unnecessary detail.

This disclosure refers to both particles and powders. These two terms are equivalent, except for the caveat that a singular "powder" refers to a collection of particles. The present invention may apply to a wide variety of powders and particles. Powders that fall within the scope of the present invention may include, but are not limited to, any of the following: (a) nano-structured powders(nano-powders), having an average grain size less than 250 nanometers and an aspect ratio between one and one million; (b) submicron powders, having an average grain size less than 1 micron and an aspect ratio between one and one million; (c) ultra-fine powders, having an average grain size less than 100 microns and an aspect ratio between one and one million; and (d) fine powders, having an average grain size less than 500 microns and an aspect ratio between one and one million.

The present invention will be readily understood by the following detailed description in conjunction with the accompanying drawings. To facilitate this description, like reference numerals designate like elements.

FIG. 1A illustrates one embodiment of a plasma spray gun 100 for use in a powder processing system. The plasma torch 100 is a DC plasma torch including a male electrode 120 and a female electrode 130. A power supply 110 is connected to the male electrode 120 and the female electrode 130 and delivers power through the plasma torch 100 by passing current across the gap 160 between the male electrode 120 and the female electrode 130. Furthermore, the plasma gun 100 includes a gas inlet 140 fluidly coupled to the gap 160 and configured to receive a working gas. The plasma gun 100 also includes a plasma outlet 150 fluidly coupled to the gap 160 on the opposite side of the plasma gun 100 from the gas inlet 140 and configured to provide a path through which a plasma powder mixture can be expelled from the plasma gun 100.

During operation, working gas flows through the gas inlet 140, through the gap 160 and out of the outlet 150. At the same time, power is supplied to the plasma gun 100. The current arcing across the gap 160 energizes the working gas and forms plasma, which flows out of the outlet 150. Powdered material is fed into the plasma stream through a powder port 170. The plasma stream entrains and works on the powder, forming a plasma powder mixture that flows out of the spray gun 100 through the outlet 150.

FIG. 1B illustrates another embodiment of a plasma spray gun 100' for use in a plasma processing system. The plasma gun 100' is a hollow electrode DC plasma gun including a hollow male electrode 120' and a female electrode 130. A power supply 110 is connected to the male electrode 120' and the female electrode 130 and delivers power through the plasma torch 100' by passing current across the gap 160 between the male electrode 120' and the female electrode 130. Furthermore, the plasma gun 100' includes a gas inlet 140' fluidly coupled to the gap 160 and configured to receive a working gas. The plasma gun 100' also includes a plasma outlet 150 fluidly coupled to the gap 160 on the opposite side of the plasma gun 100' from the gas inlet 140' and configured to provide a path through which a plasma powder mixture can be expelled from the plasma gun 100'. The plasma gun 100' further comprises a powder port 170' formed by the interior space within the hollow male electrode 120' and fluidly coupled to the gap 160, thereby allowing powder to flow through the hollow male electrode 120' and into the gap 160.

During operation, working gas flows through the working gas inlet 140', through the gap 160 and out of the outlet 150. At the same time, power is supplied to the plasma gun 100'. The current arcing across the gap 160 energizes the working gas and forms a plasma, which flows out of the outlet 150. Powdered material is fed into the plasma stream through the powder port 170' of the hollow electrode 120'. The stream entrains and works on the powder, forming a plasma powder mixture that flows out of the spray gun 100' through the outlet 150.

FIG. 1C illustrates one embodiment of a plasma spray gun 100" adapted for liquid cooling. The plasma spray gun 100" is a DC plasma gun including a male electrode 120 and a female electrode 130". A power supply (not shown) is connected to the male electrode 120 and the female electrode 130" and delivers power through the plasma gun 100" by passing current across a gap 160 between the male electrode 120 and the female electrode 130". Furthermore, the plasma gun 100" includes a gas inlet 140 fluidly coupled to the gap 160 and configured to receive a working gas. The plasma gun 100" also includes a plasma outlet 150 fluidly coupled to the gap 160 on the opposite side of the plasma gun 100" from the gas inlet 140 and configured to provide a path through which a plasma powder mixture can be expelled from the plasma gun 100". The plasma gun 100" further comprises a powder port 170" fluidly coupled to the interior of the female electrode 130".

The female electrode 130" includes features 132" 134", and 136" adapted for liquid cooling. In order to operate the plasma spray gun 100", the gun 100" is positioned within a gun body (not shown). The exemplary o-ring seals 138" and other features of the female electrode 130" are configured to prevent leakage of the liquid coolant. Generally, the gun body is configured so that liquid coolant flows in an annular path around the exterior surfaces of the female electrode 130". Specifically, coolant is channeled to an annular groove 136" formed in the front surface of the female electrode 130". A faceplate (not shown) can be fastened over the annular groove 136" to form an annular chamber through which coolant flows.

During operation, working gas flows through the working gas inlet 140, through the gap 160 and out of the outlet 150. At the same time, power is supplied to the plasma gun 100". The current arcing across the gap 160 energizes the working gas and forms a plasma, which flows out of the outlet 150. Powdered material is fed into the plasma stream through the powder port 170". The stream entrains and works on the powder, forming a plasma powder mixture that flows out of the spray gun 100" through the outlet 150. As the plasma is formed and applied to the powder, coolant flows through the annular grooves 132", 134" and 136", thereby promoting the cooling of the female electrode 130" in an attempt to avoid overheating.

Figure 2:
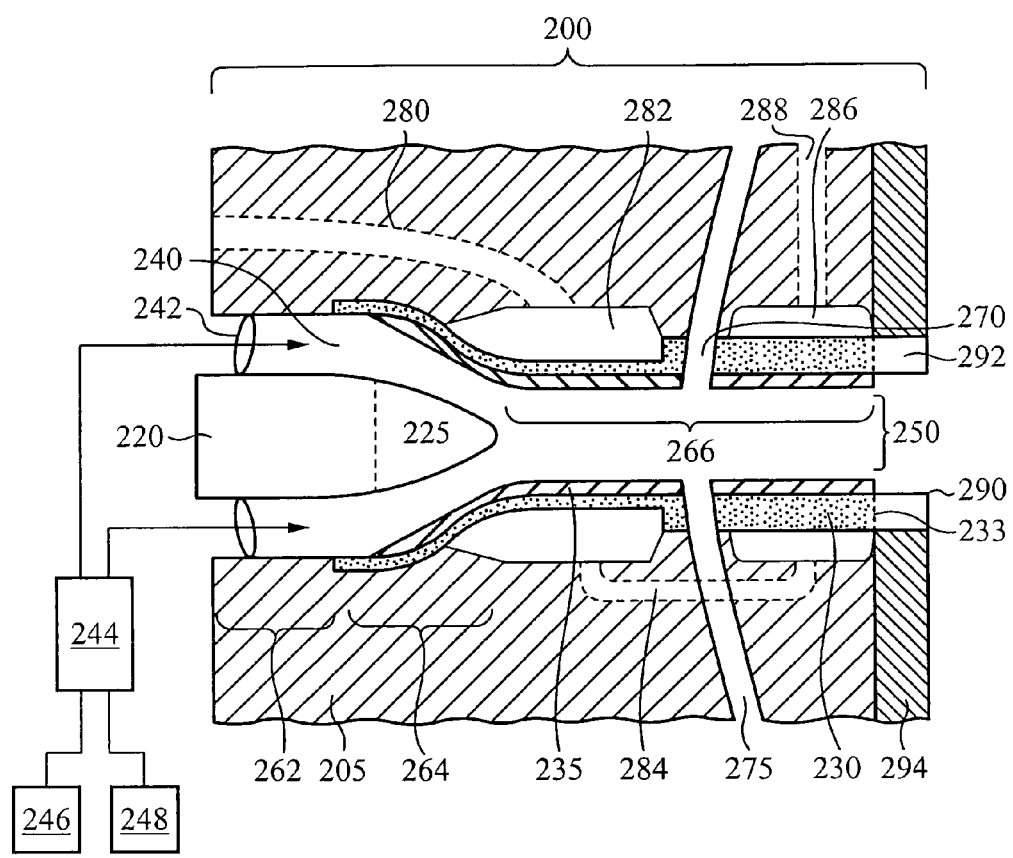
FIG. 2 is a cross-sectional schematic illustration of a plasma-arc vaporization chamber in accordance with the principles of the present invention.

FIG. 2 illustrates a plasma-arc vaporization chamber 200 in accordance with the principles of the present invention. The vaporization chamber 200 includes a male electrode 220, a female electrode 230, and a housing 205 configured to support the male electrode 220 and the female electrode 230 within a plasma gun. For clarity, only a portion of the housing 205 is illustrated. The plasma-arc vaporization chamber 200 is part of a plasma-arc vaporization system that includes energy delivery means (not shown), material delivery means (not shown), and a gas supply system 244. In a preferred embodiment, the housing 205 includes a network of coolant channels coupled with a coolant circulation system, which will be discussed in further detail below.

The male electrode 220 is preferably a cathode and includes an active end 225. In a preferred embodiment, the cathode is made of a highly conductive, durable material that is resistant to thermal breakdown. Preferably, electrical connections run from an energy delivery means to the end of the cathode 220 distal from its active end 225. In some embodiments, the male electrode 220 includes tungsten.

The female electrode 230, which is preferably an anode, defines a longitudinal axis and includes an internal chamber. In the illustrated embodiment, the housing 205 and the internal chamber of the female electrode 230 combine to form an extended internal chamber. The extended internal chamber comprises an entry region 262, a frusto-conical region 264, and an isthmus region 266. A mouth 250 provides an opening to the internal chamber. Although in the illustrated embodiment the isthmus region 266 communicates directly with the mouth 250, other embodiments having other configurations are also within the scope of the present invention. A portion of the male electrode 220 is preferably disposed within the internal chamber of the female electrode 230. Specifically, the active end 225 of the male electrode 220 is disposed within the frusto-conical region 264 of the internal chamber.

In a preferred embodiment, the surface of the internal chamber includes a target region 235 that is configured to cover at least a portion of the frusto-conical region 264 and of the isthmus region 266. This target region 235 acts as a lining to protect the interior surface of the female electrode 230 from wear caused by the plasma arc. This protection allows the plasma gun to operate at a high power and enthalpy so that full vaporization of a powder can be achieved, while at the same time minimizing the wear on the plasma gun. Preferably, the target region 235 comprises a material that is distinct from the material of the female electrode. In a preferred embodiment, the second material is a durable, highly conductive material that is resistant to thermal breakdown. One example of such a material is tungsten. However, it is contemplated that other materials can be used as well.

The female electrode 230 comprises an intermediate mouth flange surface 233 adjacent to the mouth 250. In the illustrated embodiment, a flange member 290 with a mouth flange-cooling chamber 292 is coupled to the mouth flange surface 233 of the female electrode 230. The flange-cooling chamber 292 provides a continuous annular channel adjacent to the intermediate mouth flange surface 233. Preferably, the flange-cooling chamber 292 is coupled to a network of coolant channels within the housing 205. In the illustrated embodiment, the flange-cooling chamber 292 is constructed by brazing the flange member 290 onto the female electrode 230. However, in some embodiments, the flange-cooling chamber 292 is integrally formed with the female electrode 230. Additionally, in some embodiments, the mouth 250 of the internal chamber is extended to the end of the flange-cooling chamber 292. In these embodiments, that distal end is considered the mouth flange, and is cooled by circulation of coolant through the flange-cooling chamber 292.

As briefly discussed above, a network of coolant channels within the housing 205 permits circulation of coolant around the female electrode 230. Preferably, some other channels are adjacent to the inactive end of the male electrode 220 to cool the electrode. However, these additional channels are not shown in the figures. An inlet channel 280 leads to a first coolant chamber 282, which is fluidly coupled by an intermediate channel 284 to a second coolant chamber 286. The second coolant chamber 286 fluidly communicates with an outlet channel 288. In a preferred embodiment, flange cooling chamber 292 is fluidly coupled to and configured to receive coolant from the second coolant chamber 286. In this respect, the surface of the brazed-on flange member 290 becomes the flange surface of the electrode 230, and is liquid cooled. Circulating coolant around the flange minimizes damage to the flange from high enthalpy plasma. A faceplate 294 can be coupled to a front edge of the housing 205, preferably forming a flush surface with the flange member 290.

Material transmission conduits 275 permit delivery of materials from the outer surface of the female electrode 230 through the housing 205 to material delivery ports 270 of the female electrode 230, where the materials can be introduced into the internal chamber. Preferably, the material delivery ports 270 are positioned at an angle relative to the longitudinal axis of the female electrode 230 such that material delivered therethrough has a velocity component along the longitudinal axis in the direction of the active end 225 of the male electrode 220 (i.e., in the opposite direction of the flow of the plasma.

The entry region 262 of the extended internal chamber and the male electrode 220 form one or more gas delivery channels 240, which are fluidly coupled to the rest of the extended internal chamber. In a preferred embodiment, vortexing gas injectors 242 are fluidly coupled to supply lines leading from a gas supply system 244 configured to supply working gas and are positioned to feed the working gas into the gas delivery channels 240. These vortexing gas injectors 242 are preferably configured to supply the working gas to the gas delivery channels 240 in a substantially helical pattern. The vortexing gas injectors 242 can be coupled to the housing 205. The gas supply system 244 can be fluidly coupled to a first gas storage system 246, configured to store and supply a first gas, and a second gas storage system 248, configured to store and supply a second gas. In a preferred embodiment, the first gas storage system 246 is configured to supply hydrogen, while the second gas storage system 248 is preferably configured to supply an inert gas, such as argon.

The housing 205 holds and positions the male electrode 220 and the female electrode 230 relative to one another. Furthermore, the housing preferably provides the channels for coolant circulation, materials delivery, and gas delivery discussed above.

In operation, working gas is delivered from the supply system 244 through the vortexing gas injectors 242 into the gas delivery channels 240. The vortexing stream of gas passes through the entry region 262 of the extended internal chamber, into the frusto-conical region 264, through the isthmus region 266, and out the mouth 250 of the chamber 200.

In order to produce plasma, the plasma-arc vaporization system of which the plasma-arc vaporization chamber 200 is a part delivers energy through the male electrode 220 and into the female electrode 230 (or vice versa). Preferably, an energy delivery means supplies electrical energy to the end of the male electrode 220 distal from the active end 225. This process produces an arc between the electrodes, preferably between the active end 225 of the male electrode 220 and the target region 235 of the female electrode 230. Most preferably, the arc is confined to the target region 235.

As the gas stream flows through the internal chamber between the electrodes, energy is delivered to the working gas, producing the an arc between the electrodes and forming a plasma stream from the gas stream. In a preferred embodiment, energizing of the gas begins in the frusto-conical region 264 and is completed within the isthmus region 266. Thus, a gas stream entering the gas delivery channels 240 becomes a plasma stream within the internal chamber and exits the mouth 250 as a plasma stream.

Plasma formation produces heat. In order to cool the electrodes 220 and 230, the vaporization chamber 200 can include the coolant circulation network discussed above. This network is supplied by an external coolant circulation system (not shown), which supplies coolant. In operation, coolant circulates through the inlet channel 280, into the first chamber 282, through the intermediate channel 284, and into the second chamber 286. Fluid from the second chamber 286 exits through the outlet channel 288. Furthermore, fluid from the second chamber 286 preferably circulates into the flange-cooling chamber 292. In a preferred embodiment, fluid flows between the second chamber 286 and the flange-cooling chamber 292 through channels within the female electrode 230.

Preferably, the material transmission conduits 275 are fluidly coupled with a material supply system (not shown) that provides a metered flow of material into the conduits 275. In order to begin vaporizing a material, the material supply system provides material, preferably in the form of powder, to the conduits 275. In a preferred embodiment, the material delivery ports 270 are angled so that they deliver material along a vector that has a component opposite the direction of gas flow within the internal chamber. Material travels through the conduits 275 into the material delivery ports 270, which lead to the isthmus region 266 of the internal chamber.

Many embodiments of the present invention include features selected to increase resonance times for delivered materials. The resonance time relates to the amount of time the delivered material is maintained within a plasmatic environment. Furthermore, some embodiments include features to permit higher plasma energies. By increasing resonance times and permitting higher energy plasmas, the embodiments of the present invention are capable of vaporizing much higher vapor point materials within the internal chamber than are other plasma spray guns.

One way the present invention increases resonance time is by flowing the powder from the ports 270 into the stream of plasma at an angle across the flow of the stream. Preferably, the powder flows into the internal chamber and plasma stream at an angle of at least 20 degrees (measured from a plane perpendicular to the flow of the plasma stream). By delivering material at an angle against the flow of the plasma stream, instead of perpendicular to or angled with the flow, the vaporization chamber 200 increases the resonance time for each material particle. This increase in resonance time allows for the full vaporization of higher vapor point materials to take place.

Another way the present invention increases resonance time is by employing an isthmus region 266 with a width that is sufficiently large to permit vaporization of material delivered through the material delivery port 270 and into the isthmus region 266 during operation of the chamber 200. By using a large width isthmus region 266, the vaporization chamber 200 slows down the plasma stream, thereby increasing resonance times for delivered materials. In a preferred embodiment, the isthmus region has a diameter of at least 0.400 of an inch, thereby providing a significant increase in bore diameter, and thus resonance time, over other vaporization chambers. While the isthmus region preferably has a diameter of at least 0.400 of an inch, in some embodiments the diameter may be restricted to a maximum of 0.500 of an inch in order to avoid a conflict with the coolant channels and chambers.

Some embodiments of the present invention include features to permit increased plasma energies. Increasing plasma energy typically means increasing the amount of energy delivered between the electrodes 220 and 230, increasing the flow rate of the plasma, or varying the composition of the gas. For example, the features included within the present invention permit use of plasmas with energies of above 1000 amperes. Additionally, the present invention preferably employs plasmas having a high hydrogen content. In a preferred embodiment, the present invention employs plasmas having a high hydrogen content and flow rates of more than 5 liters per minute, resulting in at least 43 volts (at least 43 kilowatts when run at energies above 1000 amperes). The hydrogen can be supplied in the working gas. Plasmas with such characteristics stress the electrodes 220 and 230 by increasing the enthalpy of the plasma stream, and by demanding that the electrodes transmit greater amounts of electrical energy.

Traditional female electrodes use a mono-material construction. However with increased plasma energies, thermal durability of the electrode's internal surface becomes more important. Hence, the present invention provides the target material 235 as part of the female electrode 230. The target material 235 is preferably a durable, conductive material that is highly resistant to thermal breakdown. However, in a preferred embodiment, the entire electrode is not constructed from the target material 235. Only a portion of the electrode comprises the target material 235. Preferably, the male electrode 220 and the female electrode 230 are configured so that during normal operation, an arc passing from the active end 225 of the male electrode 220 to the female electrode 230 will ground through the target material 235. The target material 235 acts as a lining to protect the female electrode 230 from wear. In a preferred embodiment, the target material 235 comprises tungsten.

In the preferred mode of operation, the arc between the electrodes 220 and 230 moves around to various locations on the female electrode 230. However, as the plasma energy increases, the frequency of these movements must increase to avoid pitting of the electrode 230. In other words, the higher the energy of the arc, the shorter the time it takes to vaporize the electrode material when concentrated in a single location. Thus, the arc settling time, i.e., the resting time between movements of the arc, must decrease to avoid or minimize degradation of the electrode.

In order to increase the frequency of arc movements, some embodiments of the present invention include the vortexing gas injectors 242. In a preferred embodiment, the vortexing gas injectors 242 are configured to deliver the working gas into the frusto-conical region 264 between the male electrode 220 and the female electrode 230 in a substantially helical pattern. Preferably, within this helical pattern, the highest gas velocities are at angles to the longitudinal axis of the female electrode 230. The helical pattern increases the mass flow rate of the gas relative to the volume flow rate of the gas (both measured along a direct path through the internal chamber).

Additionally, at higher plasma energies, the plasma stream exits the mouth 250 of the vaporization chamber 200 with a higher enthalpy. Without the brazed-on flange member 290, this higher enthalpy could lead to overheating or melting of the intermediate flange surface 233 of the female electrode 230. In order to alleviate this problem, the female electrode 230 includes the brazed-on flange member 290, which is configured to receive coolant, preferably from the second coolant chamber 286. Thus, the surface of the brazed-on flange member 290 becomes the flange surface of the electrode 230, and is liquid cooled. Circulating coolant around the flange minimizes damage to the flange from high enthalpy plasma. It is contemplated that coolant may optionally be supplied directly to the cooling chamber 292 of the flange member 290 without any need for the other coolant channels or chambers.

Embodiments of the present invention are extremely beneficial in achieving full vaporization of powders having a mean grain size up to an including 10 microns. The best results are achieved when employing all of the features discussed above (counter-flow angled powder injection, wide diameter bore, target material lining, vortexing gas injectors, and flange coolant chamber). However, it is contemplated that any combination of these features will result in substantial improvements over the prior art.

Figure 3:
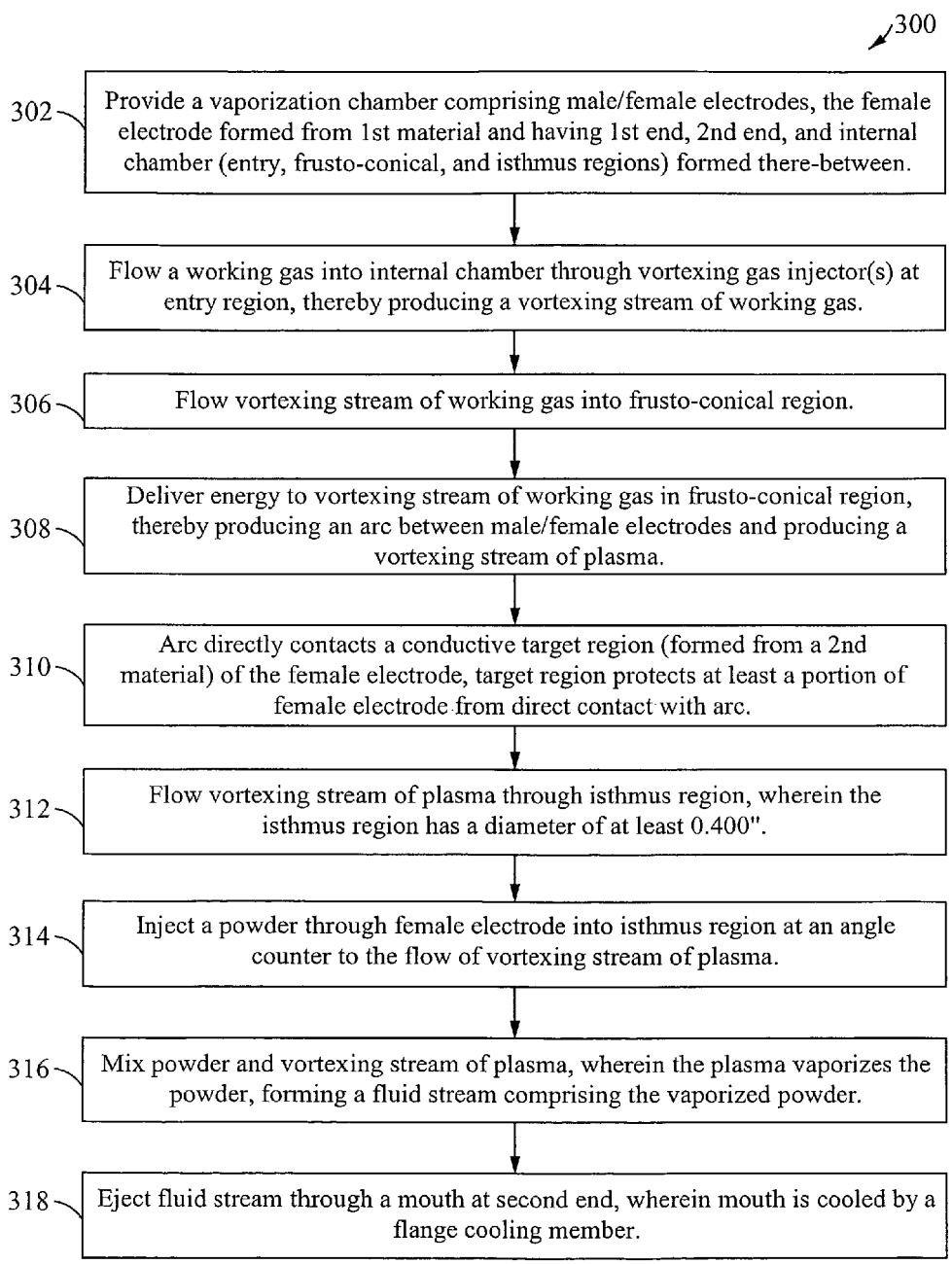
FIG. 3 is a flow chart illustrating one embodiment of a method of vaporizing powder in the plasma-arc vaporization chamber in accordance with the principles of the present invention.

FIG. 3 is a flow chart illustrating one embodiment of a method 300 of vaporizing powder in a plasma-arc vaporization chamber in accordance with the principles of the present invention. As would be appreciated by those of ordinary skill in the art, the protocols, processes, and procedures described herein may be repeated continuously or as often as necessary to satisfy the needs described herein. Additionally, although the steps of method 300 are shown in a specific order, certain steps may occur simultaneously or in a different order than is illustrated. Accordingly, the method steps of the present invention should not be limited to any particular order unless either explicitly or implicitly stated in the claims.

At step 302, a vaporization chamber, such as vaporization chamber 200 described above, is provided. The vaporization chamber comprises a male electrode and a female electrode supported within a housing member. The female electrode is formed from a first material and has a first end, a second end opposite the first end, and an internal chamber. The internal chamber extends from an entry region at the first end through a frusto-conical region to an isthmus region. The isthmus region preferably extends all the way to the second end of the female electrode.

At step 304, a working gas flows into the internal chamber through one or more vortexing gas injectors disposed at the entry region, thereby producing a vortexing stream of working gas. In a preferred embodiment, the vortexing gas injectors produce the vortexing stream of working gas in the form of a helical pattern. Preferably, the working gas has a high hydrogen content.

At step 306, the vortexing stream of working gas flows into the frusto-conical region, in between the male electrode and the female electrode.

At step 308, energy is delivered to the vortexing stream of working gas in the frusto-conical region, thereby producing an arc between the male electrode and the female electrode and producing a stream of plasma. It is contemplated that the arc can be produced in a variety of ways. In a preferred embodiment, an energy delivery means delivers energy through the male electrode and into the female electrode (or vice versa). This process produces an arc between the electrodes. In a preferred embodiment, this stream of plasma substantially maintains its vortexing or helical pattern.

At step 310, the arc directly contacts a conductive target region of the female electrode. The target region is formed from a second material, distinct from the first material of the female electrode, that is highly durable and conductive, such as tungsten. The target region acts as a lining that protects at least a portion of the first material of the female electrode. Preferably, the target region protects the rest of the female electrode from any direct contact with the arc. In some embodiments, the target region can be removable from the first material of the female electrode.

At step 312, the stream of plasma flows through the isthmus region. The isthmus region has a diameter of at least 0.400" in order to reduce the velocity of the plasma stream, thereby increasing the resonance time.

At step 314, a powder is injected, preferably through a conduit in the female electrode, into the isthmus region of the internal chamber. The powder is injected at an angle counter to the flow of the stream of plasma. In a preferred embodiment, the powder flows into the isthmus region and the plasma stream at an angle of at least 20 degrees. This angle is pitched towards the entry region and is measured from a plane perpendicular to the flow of the plasma stream.

At step 316, the powder is mixed with the stream of plasma. The stream of plasma vaporizes the powder, thereby forming a fluid stream comprising the vaporized powder. In a preferred embodiment, the injected powder is fully vaporized. The present invention preferably employs plasmas with energies above 1000 amperes and a high hydrogen content. In a preferred embodiment, the present invention flows the plasma at rates of more than 5 liters per minute, resulting in at least 43 volts (at least 43 kilowatts when run at energies above 1000 amperes).

At step 318, the fluid stream containing the vaporized powder is ejected from the internal chamber through a mouth disposed at the second end of the female electrode. The mouth is cooled by a flange cooling member disposed adjacent to the mouth. In a preferred embodiment, the flange cooling member comprises a coolant chamber as discussed above.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made to the embodiments chosen for illustration without departing from the spirit and scope of the invention.

What is claimed is:

1. A vaporization chamber comprising:
   a male electrode;
   a female electrode comprising a first material, the female electrode having a first end, a second end opposite the first end, and an internal chamber formed within the female electrode in between the first end and the second end, wherein the internal chamber comprises an entry region, a frusto-conical region, and an isthmus region, the entry region being disposed at the first end and configured to receive a working gas, the frusto-conical region extending from the entry region to the isthmus region, wherein the isthmus region has a diameter of at least 0.400 of an inch and extends to the second end along a longitudinal axis of the female electrode, the second end forming a mouth through which a fluid can exit the internal chamber along the longitudinal axis;
   a vortexing gas injector disposed proximate the first end and fluidly coupled to the entry region of the internal chamber, wherein the vortexing gas injector is configured to receive a working gas, to produce a vortexing stream of the working gas, and to supply the vortexing stream of working gas to the frusto-conical region of the internal chamber;
   a combustible gas supply system fluidly coupled to the vortexing gas injector, wherein the combustible gas supply system provides a combustible gas as at least a portion of the working gas to the vortexing gas injector;
   an electrical connection point disposed on at least one of the male electrode and the female electrode, wherein the electrical connection point is configured to deliver energy to the vortexing stream of working gas in the frusto-conical region upon receiving power from a power supply, thereby producing an arc capable of fully vaporizing powders between the male electrode and the female electrode within the frusto-conical region of the internal chamber and producing a vortexing stream of plasma that flows into the isthmus region;
   a target region configured to act as lining for the female electrode in at least a portion of the frusto-conical region and in at least a portion of the isthmus region of the internal chamber, wherein the target region comprises a second material that is distinct from the first material and that is conductive, and the target region is configured to protect at least a portion of the female electrode from direct contact with the arc;
   a material delivery port configured to deliver powder into the isthmus region of the internal chamber at an angle counter to the flow of the vortexing stream of plasma; and
   a mouth flange cooling chamber disposed at the second end of the female electrode adjacent to the mouth, wherein the mouth flange cooling chamber is configured to permit circulation of cooling fluid around the longitudinal axis, thereby cooling the mouth when plasma exits the internal chamber.

2. The vaporization chamber of claim 1, further comprising a housing supporting the male electrode and the female electrode.

3. The vaporization chamber of claim 2, wherein the mouth flange cooling chamber is brazed onto the second end of the female electrode.

4. The vaporization chamber of claim 3, further comprising a network of coolant channels disposed within the housing, wherein the network of coolant channels is configured to permit circulation of coolant around the female electrode and into the mouth flange cooling chamber.

5. The vaporization chamber of claim 1, wherein the isthmus region has a maximum diameter of 0.500 of an inch.

6. The vaporization chamber of claim 1, wherein the target region comprises tungsten.

7. The vaporization chamber of claim 1, wherein the material delivery port is configured to deliver the powder into the isthmus region of the internal chamber at an angle pitched at least 20 degrees towards the entry region measured from a plane perpendicular to the flow of the vortexing stream of plasma.

8. The vaporization chamber of claim 1, wherein the combustible gas comprises hydrogen.

9. The vaporization chamber of claim 8, wherein
   a power supply is connected to the electrical connection point and configured to produce a vortexing stream of plasma having an electric current greater than 1000 amperes; and wherein the vaporization chamber further comprises a working gas supply system configured to supply the working gas at a flow rate greater than 5 liters per minute.

10. The vaporization chamber of claim 1 further comprise a working gas supply system fluidly coupled to the vortexing gas injector, wherein the working gas supply system provides inert gas as at least a portion of the working gas to the vortexing gas injector.

11. A vaporization chamber comprising:
    a male electrode;

a female electrode comprising a first material, the female electrode having a first end, a second end opposite the first end, and an internal chamber formed within the female electrode in between the first end and the second end, wherein the internal chamber comprises an entry region, a frusto-conical region, and an isthmus region, the entry region being disposed at the first end and configured to receive a working gas, the frusto-conical region extending from the entry region to the isthmus region, wherein the isthmus region has a diameter of at least 0.400 of an inch and extends to the second end along a longitudinal axis of the female electrode, the second end forming a mouth through which a fluid can exit the internal chamber along the longitudinal axis;

a gas inlet disposed proximate the first end and fluidly coupled to the entry region of the internal chamber, wherein the gas inlet is configured to receive a working gas and to supply the working gas to the frusto-conical region of the internal chamber;

a hydrogen supply system fluidly coupled to the gas inlet, wherein the hydrogen supply system provides hydrogen gas as at least a portion of the working gas to the gas inlet;

an electrical connection point disposed on at least one of the male electrode and the female electrode, wherein the electrical connection point is configured to deliver energy to the working gas in the frusto-conical region upon receiving power from a power supply, thereby producing an arc capable of fully vaporizing powders between the male electrode and the female electrode within the frusto-conical region of the internal chamber and producing a stream of plasma that flows into the isthmus region;

a target region configured to act as lining for the female electrode in at least a portion of the frusto-conical region and in at least a portion of the isthmus region of the internal chamber, wherein the target region comprises a second material that is distinct from the first material and that is conductive, and the target region is configured to protect at least a portion of the female electrode from direct contact with the arc;

a material delivery port configured to deliver powder into the isthmus region of the internal chamber to mix with the stream of plasma; and a mouth flange cooling chamber disposed at the second end of the female electrode adjacent to the mouth, wherein the mouth flange cooling chamber is configured to permit circulation of cooling fluid around the longitudinal axis, thereby cooling the mouth when plasma exits the internal chamber.

* * * * *